United States Patent [19]

Buck

[11] Patent Number: 5,512,275
[45] Date of Patent: Apr. 30, 1996

[54] TOPICAL LOTION AND METHOD FOR TREATMENT OF ANDROGENIC ALOPECIA

[76] Inventor: Carol J. Buck, 30 Brooks Bend, Princeton, N.J. 08540

[21] Appl. No.: 343,647

[22] Filed: Nov. 22, 1994

[51] Int. Cl.[6] .......................... A61K 7/06; A61K 31/19; A61K 31/22; A61K 31/125
[52] U.S. Cl. .......................... 424/70.1; 514/549; 514/568; 514/692; 514/880
[58] Field of Search ..................... 514/547, 568, 514/692, 880, 549; 424/70.1

[56] References Cited

U.S. PATENT DOCUMENTS

| | | | |
|---|---|---|---|
| 3,766,052 | 10/1973 | Berdovsky et al. | 208/45 |
| 3,928,579 | 12/1975 | McShane | 424/167 |
| 4,102,995 | 7/1978 | Hebborn | 424/81 |
| 4,178,373 | 12/1979 | Klein et al. | 424/233 |
| 4,832,946 | 5/1989 | Green | 424/70 |
| 4,849,214 | 7/1989 | Ruiseco | 424/74 |
| 5,081,151 | 1/1992 | Davis et al. | 514/574 |
| 5,130,142 | 7/1992 | Wong et al. | 424/574 |
| 5,158,955 | 10/1992 | Gibson et al. | 514/272 |
| 5,185,325 | 2/1993 | Brawn et al. | 514/23 |
| 5,192,534 | 3/1993 | Grollier et al. | 424/59 |

FOREIGN PATENT DOCUMENTS 3633242  4/1988  Germany.

*Primary Examiner*—Marianne M. Cintins
*Assistant Examiner*—Phyllis G. Spivack
*Attorney, Agent, or Firm*—Mathews, Woodbridge & Collins

[57] ABSTRACT

A formulation and method of treatment for androgenic alopecia wherein the active ingredient is liquor carbonis detergens, in combination with spirits of camphor, castor oil, isopropyl alcohol, and optionally salicyclic acid.

10 Claims, 2 Drawing Sheets

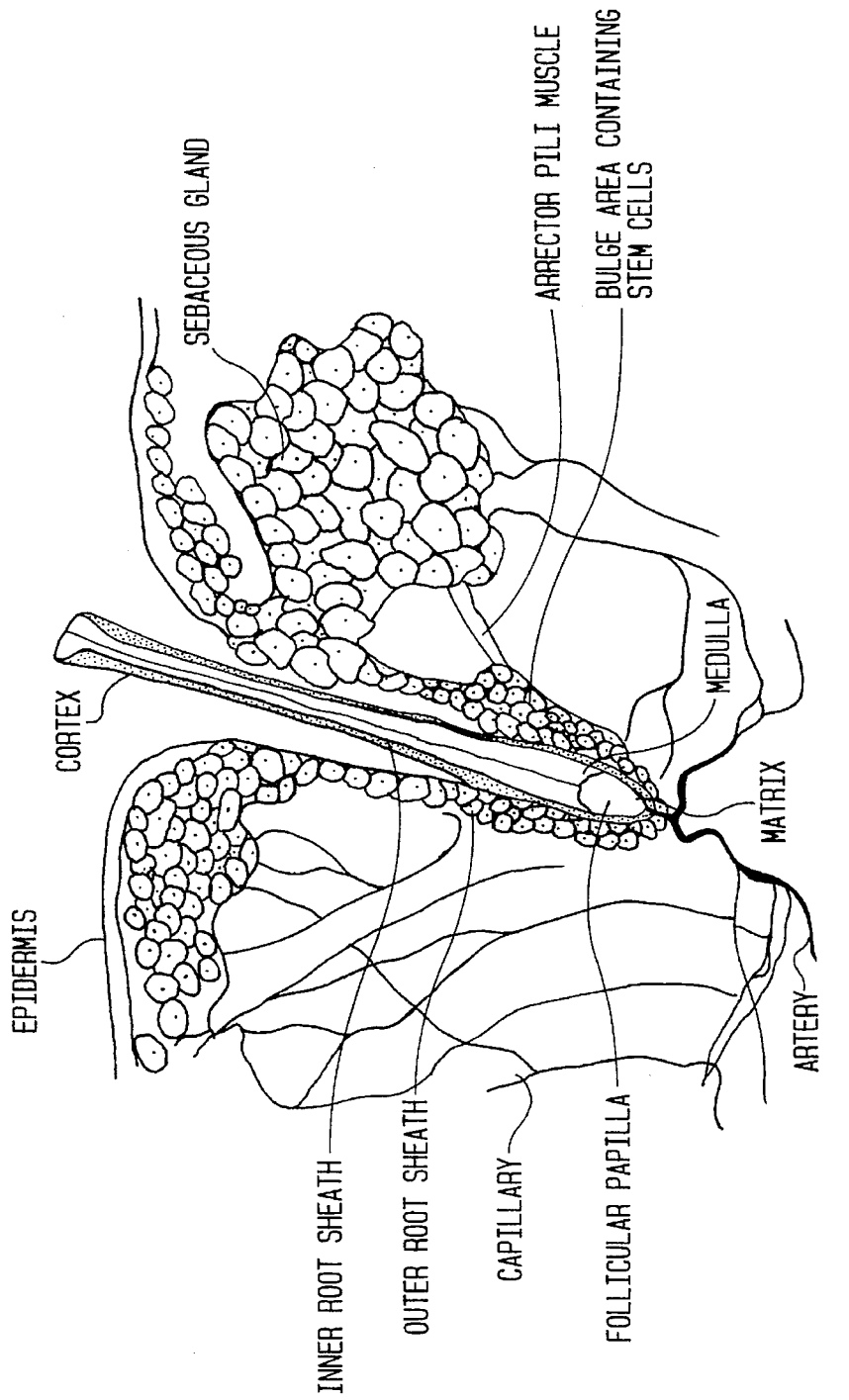

TOPICAL LOTION AND METHOD FOR TREATMENT OF ANDROGENIC ALOPECIA

This invention pertains to a topical lotion and method for treatment of androgenic alopecia.

BACKGROUND OF THE INVENTION

THE HAIR GROWTH CYCLE

In most mammals, hair does not grow continuously, but undergoes a cycle of activity involving periods of growth, rest and shedding. On the human scalp, from 100,000 to 350,000 hair fibers or shafts undergo metamorphosis in three distinct stages, namely:

(i) the growth phase, known as anagen, during which the hair root bulb or dermal papilla (also called the "follicular papilla") penetrates deep into the dermis with the cells of the bulb dividing rapidly and differentiating in the process of synthesizing keratin, the substance of the hair shaft itself. In normal humans, this growth phase is thought to last from one to five years;

(ii) the transitional stage, catagen, is marked by the cessation of mitosis. This phase lasts from two to three weeks; and (iii) the resting stage known as telogen, where the hair is retained within the scalp for up to 12 weeks before the emerging new hair developing below it dislodges the telogen-phase shaft from its follicle.

For reasons yet unknown, subjects evidencing androgenic alopecia experience gradual changes in the width and length of the hair shaft over time and with age, some prematurely. Men as early as their 20's and women in their 30's and 40's begin to notice their hair becoming finer and shorter. In addition, the ratio of growing hairs to hairs in the resting/shedding phase declines from as high as 9:1 to as low as 2:1. Exactly how and where the growth and regenerative processes is damaged has yet to be definitively understood.

It is generally accepted that genetic hair loss arises from the activation of an inherited predisposition to circulating androgenic hormones. Androgenic alopecia is the single largest type of recognizable alopecia to affect both men (50%) and women (30%), primarily of Caucasian origin. The condition is characterized by the gradual conversion of terminal hair to short, wispy, colorless vellus hair. FIGS. 1 and 2 compare a healthy terminal hair follicle to one transformed by androgenic alopecia into a vellus hair.

While many investigators have tried to isolate the causative androgen metabolite, no single molecule has emerged. Nor, in comparative studies between nonbalding controls, has a significant difference between mean hormonal values or amounts been detected. See J. Puolakka, Serum ferritin in the evaluation of iron status in young health women, Acta. Obsteto Gynecol. Scand. suppl. 95, 35–41 (1980). This suggests that a sensitivity or receptivity to hormones at the cell binding sites within the dermal papilla is a possible factor. Several treatments are based on this theory using anti-androgens such as CPA (cyproterone acetate) in combination with ethinyl-estradiol and the aldosterone antagonist spironolactone, which, given in dosages from 75 to 100 mg per day has shown some benefit. See e.g., D. H. Rushton and D. D. Ramsay, The importance of adequate serum ferritin levels in cyproterone acetate and ethinyl-oestradiol therapy in women with diffuse androgen-dependant alopecia, Clin. Endocrinol. 36, 421–427 (1992); DH Rushton, W. Futterwiet, DH Kingsley, P. Kingsley and MJ Norris, Quantitative assessment of spironolactone treatment in women with diffuse androgen-dependent alopecia, J. Soc. Cosmet. Chem. 42, 317–325 (1991).

Prior art also includes mucopolysaccharide and chondroitin sulfate in hair compositions to prevent loss and encourage growth. However, according to The Berkeley Wellness Letter, published by the University of California (June 1992, vol. 8 no. 9 pg. 4), the treatment philosophy for genetic hair loss depends predominantly upon controlling the testosterone metabolite, DHT (dihydrotestosterone). The major bio-synthetic pathway of DHT is catalyzed by the enzyme 5[alpha]-reductase. It is hypothesized by these researchers that compounds which selectively block this enzyme (by inhibiting substrate uptake or altering the binding affinity for the androgen receptor protein complex) could have a high success rate at halting premature anagen termination. In this regard, Brawn et al. (U.S. Pat. No. 5,185,325) has developed a topical application containing a glycosaminoglycanase inhibitor chosen from aldonomonolactones, alduronomonolactones and acylated monosaccharides. They identify the breakdown of glycosaminoglycans (complex polysaccharides) by male hormones as the initiating condition of the onset of catagen. This approach attempts to sustain hair growth by preventing the splitting of the glycosaminoglycan molecule at specific sites by the topical application of certain molecules such as asacylated monosaccharides. Brawn foresaw a 10% to 50% increase in hair growth versus the control. Clinical human trial data was not supplied in the patent.

As illustrated in FIG. 1, experiments with mouse hair follicles showed that the anagen phase stem cells, stored within the bulge area of the follicle, proliferated during early anagen and migrated to the root bulb region prior to differentiation. See Miller, Stanley J., Sun, Tung-Tien, and Lavker, Robert M., Hair Follicles, Stem Cells, and Skin Cancer, The Society for Investigative Dermatology, 1993. Miller et al. believe that the bulge cells can be stimulated to proliferate in response to both physical and chemical stimuli causing telogen follicles to commence anagen. In addition, the physical proximity of the follicular papilla to the bulge area containing the stem cells plays a role in the onset of anagen cycles. Miller et al. have speculated that damage to the bulge region (such as is caused by lupus erythematosus or lichen planopilaris) frequently results in permanent alopecia, whereas damage to the hair root bulb alone results in alopecia areata and is temporary.

It is noted that several of the ingredients such as salicylic acid and castor oil have been employed as hair growth stimulants. Their therapeutic functions are identified as emollients (castor oil) and irritants and keratolytics for the stimulation of blood flow (salicylic acid and spirits of camphor).

U.S. Pat. No. 5,081,151, issued to Davis, et al. relates to a method for inducing, maintaining or increasing hair growth by topically applying a preserved composition comprising an effective amount of hexosaccharic acid, salts and esters thereof.

U.S. Pat. No. 5,158,955 issued to Gibson, et al. relates to a preserved composition for topical application for inducing, maintaining or increasing hair growth which comprises a special ester of pyroglutamic acid and a cosmetically acceptable vehicle for the ester. Gibson lists salicylic acid and castor oil as hair growth stimulants. Isopropyl alcohol is also disclosed.

U.S. Pat. No. 5,185,325, issued to Brawn, et al. relates to a composition for inducing, maintaining or increasing hair growth including a glycosaminoglycanase inhibitor chosen from aldonomonolactones, alduronomonolactones and acylated monosaccharides. Brawn discloses the use of salicylic acid and castor oil as substances which stimulate or increase hair growth, and the use of penetration enhancers, such as isopropyl alcohol.

U.S. Pat. No. 4,849,214, issued to Ruiseco relates to an oil based composition for the treatment of dry scalp conditions, which includes grated avocado seed in a mineral oil solution and the addition of other ingredients, such as castor oil and spirit of camphor.

U.S. Pat. Nos. 5,130,142, issued to Wong, et al., relates to a composition for regulating hair growth which includes a supernatant derived from a culture of epithelial cells. When the composition is in lotion or cream form, it can include emollients (such as castor oil) and additionally alcohol.

U.S. Pat. No. 5,192,534, issued to Grolier, et al. relates to compositions for inducing and stimulating hair growth and/or retarding its loss containing, in combination, pyrimidine derivatives and at least some agents which screen out UV radiation.

It is also known that liquor carbonis detergens has been established as a treatment for certain skin disorders (See e.g., U.S. Pat. Nos. 4,102,995; 3,627,871; 3,472,931; 3,061,512; 3,071,510; 23,262,851; 2,622,057; and 2,602,039) and is especially effective as an antipruritic, antibacterial and keratoplastic (control of the production of epithelial keratin) in the treatment of psoriasis, often formulated as a shampoo. Nowhere, however, in the prior art of commercial or non-commercial compositions is there a reference to the use of liquor carbonis detergens as a therapy for hair loss alone or in combination with any of the ingredients identified.

A recent study conducted in Cologne, Germany [Merk, H.F., Mukhtar, H., Schutte, B. et al., Department of Dermatology, University of Cologne] identified a high correlation (95%) of enzyme activation within the cells of the follicular papilla when a solution of liquor carbonis detergens was topically applied to freshly plucked roots. The researcher suggested that the cytochrome P-450 isozymes, affecting the metabolism of oxygen within the cell, was altered by this solution. It was also theorized by Levkar et al., in his study of the origin of skin cancers that most non-melanoma cancers of the skin originate in the hair follicle, suggesting that the cells of this region are more highly prone to mitosis than epithelial cells between the follicles. In fact, during the entire anagen phase the cellular activity, both in terms of migration and mitosis, is highly active, resulting in the proliferation of keratinocytes (the cells of the shaft itself).

Minoxidil (Rogaine) therapy

In the late 1980's the Upjohn Company received FDA approval to market Rogaine as an antibaldness therapy. Rogaine has met with limited commercial and clinical success. Its active ingredient, a 2% solution of minoxidil (originally prescribed as an antihypertension medication), is marketed under prescription for about $50/month as a topical solution. While retardation of hair loss is widely reported (90%), actual new hair growth occurs among only 10% to 15% of the cases. Older men are less likely to see results than younger ones, and hair regrowth is reported only on the crown portion of the scalp. Compounding the low regeneration rate is the risk of subjects developing heart lesions, headaches, weight gain and facial hair (among women) with continued use. The condition is also chronic. Once twice-daily Rogaine applications are discontinued, the newly-grown hair dies and falls out and general hair loss continues. The regimen costs about $600 per year.

The new use, retardation of androgenic alopecia, for the formula that is the subject of this application is supported by the findings of the Rogaine clinical trials which showed that when the hair follicle receives more blood it is capable of resisting the damaging effects of androgens and will sustain its size and productivity. Without this daily stimulus, however, follicles return to their accelerated aging process and shrink in size and regenerative duration. This invention will begin its own clinical trials in early 1995 and expects to demonstrate at least parity in retardation of effluvium to Rogaine with the advantages of increased safety and the anticipation of a significantly lower retail price as an OTC product. However, Rogaine has several limitations and label warnings which make it inadvisable for much of the alopecia patient population:

1) It has never been tested on older adults or pregnant women.

2) It is not advised for people with skin problems or scalp irritation, heart disease or hypertension. For these individuals, excessive absorption of minoxidil may lead to chest pain, fast or irregular heartbeat, flushing, headaches, numbness or tingling of the hands, feet or face, swelling of feet or lower legs and rapid weight gain.

Upjohn has researched higher levels of minoxidil (up to 5%) as well as the addition of Retin-A to increase absorption and found that both result in higher satisfaction rates with the treatment. However, Retin-A is a strong skin irritant and the high dosage of minoxidil carries with it increased risk of heart tissue damage. Nevertheless, Rogaine is the prescription of choice by most dermatologists for androgenic alopecia.

BRIEF DESCRIPTION OF THE FIGURES

FIG. 2 shows the vellus human hair follicle after androgenic alopecia.

DETAILED DESCRIPTION

Figure 1:
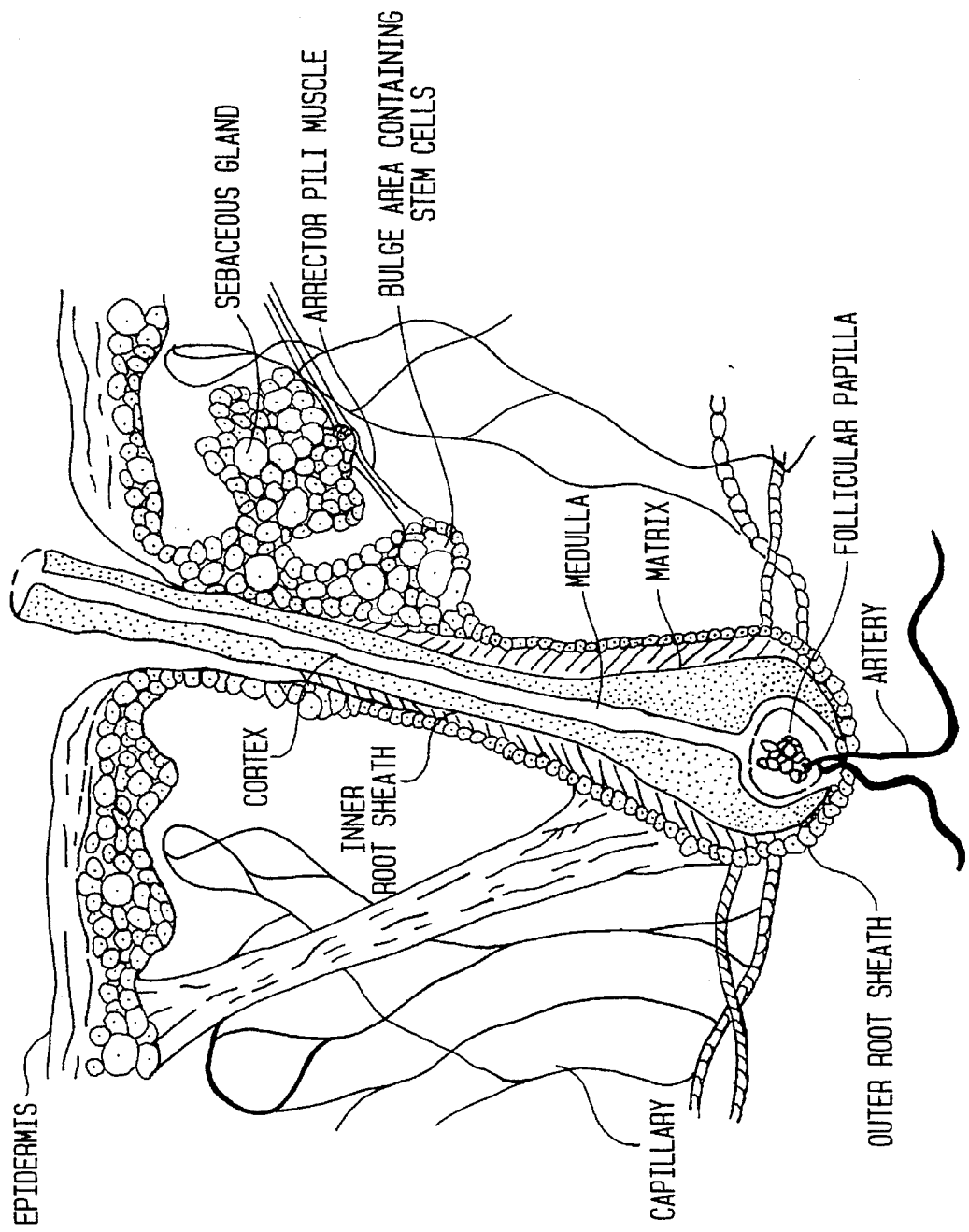
FIG. 1 shows the healthy terminal human hair follicle, and relevant components.

This present patent application pertains to a use of a coal tar formulation, in combination with other named and related ingredients to help sustain the hair shaft's growth cycle in the anagen phase and assist in the formation of new shafts. The exact mechanism by which this is accomplished is not known by the inventor, however, the medicinal affects of coal tar for the treatment of psoriasis have been well established, as discussed above, and are known to have a metabolic effect on skin cells, including the epidermal layer of the scalp. The remaining ingredients assist in the delivery of the liquor carbonis detergens to the dermal papilla by acting as fat/oil emollients, stimulants, and other supporting agents as discussed below.

The invention includes liquor carbonis detergens and may include salicylic acid, spirits of camphor, castor oil, isopropyl alcohol and, other adjuvants, analogues, cosmetic perfumes, derivatives and agents, such as Retin-A, Minoxidil, known or claimed to retard hair shedding or regenerate growth or support those processes, such as: CPA (Cyproterone acetate), growth stimulating factors (supernatants), sulfates, pyrimidines, hexosaccharic acid, salts and esters thereof, pyroglutamic acid and esters thereof, and anti-androgens.

It is hypothesized that any one of several biochemical cellular and molecular disturbances that occur during the anagen phase or catagen phase of subjects with androgenic alopecia are corrected or improved metabolically either in the functioning or formation of the stem cells, their migration process or during the mitosis phase of keratin production within the follicular papilla and matrix.

Formula Composition

A preferred embodiment for the present invention is a composition with the following component percentages:

| Component | Parts of solution | % |
| --- | --- | --- |
| Liquor carbonis detergens (coal tar) | 8 | 4.4 |
| Salicylic acid | 2 | 1.1 |
| Spirits of Camphor | 30 | 16.7 |
| Castor Oil (or similar oil) | 2 | 1.1 |
| Isopropyl alcohol | 138 | 76.7 |
| Perfume (Range) | | |
| Adjuvents* | | |
| total | 180 | 100.0 |

*Such as, Minoxidil, Retin-A, CPA (Cyproterone acetate), growth stimulating factors (supernatants), sulfates, pyrimidines, hexosaccharic acid, salts and esters thereof, pyroglutamic acid and esters thereof, and anti-androgens, which can be factored in as desired.

However, the formulation can be within the following ranges:

Liquor Carbonis Detergens, from about 0.01% to about 5%

Salicylic acid, 0–2%

Spirits of Camphor, 0–20%

Castor Oil or similar oil, 0–7%

Isopropyl Alcohol (70% alcohol, 30% water), 60–95%

Adjuvants and cosmetics as desired.

The action and function of the ingredients for the treatment of alopecia by topical application to the scalp are as follows:

Liquor carbonis detergens (LCD) is a light-yellow, thin, oily liquid form of coal tar, also called pixabol, which is a by-product in the destructive distillation of coal. LCD is an amalgam constituted of benzene, toluene, naphthalene, anthracene, zyleen and other aromatic hydrocarbons; phenol, cresol, and other phenol bodies; ammonia, pyridine, and some other organic bases; and thiophenean.

Liquor Carbonis Detergens (an alcohol extract of crude coal tar) is traditionally characterized as a thin lubricant and moisturizing agent capable of mechanically separating epithelial cells resulting in a loosening and softening (also called desquamation) of skin scales and crusts softens the scales and crusts, and helps correct abnormalities of keratinization by decreasing epidermal proliferation and dermal infiltration. Liquor carbonis detergens also has antiseptic qualities derived from its substituted phenols and works as a minor irritant, stimulating the capillaries to increase blood flow to the follicular papilla.

LCD may function as an inhibitor of enzyme catalytic activity in a number of ways. Among them, LCD could either degrade, polarize, or cause physical or chemical changes to enzymes such that their effect upon the cells of the follicular papilla and elsewhere becomes diminished. Since enzymes are also denatured by changes to the pH level, it is possible that coal tar alters the pH level in the dermal papilla (where enzymes are active) from the normal neutral to slightly alkaline state (7.8 to 8.1) to a more acidic level, thereby compromising the functioning of the androgen enzymes which are believed by many to be responsible for alopecia.

Coal tar has long been known to block cell uptake of Vitamin D which, in turn, permits penetration of UV light radiation as a therapy for psoriasis and shingles. This inventor would suggest that coal tar's efficacy in retarding alopecia is based upon a different androgen blocker reaction, that of hormonal activity suppression.

LCD's possible role in the metabolic functions of oxygen-carrying isozymes within the cell and in the migration of stem cells from the bulge region to the follicular papilla are also identified and will be clinically explored along with enzyme reactions.

Salicylic acid works as a blood flow stimulant and as a keratolytic agent, bactericide and an adjunct in fungal infections which may be present on the scalp and inhibiting the normal functioning of the hair root bulb. Salicylic acid also serves to dissolve skin oils and reduce their viscosity within the sebaceous glands and ducts.

Spirits of Camphor (dissolved crystals) is a mild rubefacient, analgesics antiseptic and antipruritic with mildly irritating and stimulating properties affecting capillary action.

Isopropyl Alcohol (Isopropanol) serves as a solvent of surface oils, antiseptic, stimulant of blood flow, and media in which the other ingredients are dissolved.

Oil of Ricine (castor oil) is used to improve the regrowth or epithelialization of skin cells by reducing premature epithelial desiccation and cornification. It also acts as a protective covering to the irritated surface skin cells.

While the exact interaction of the above ingredients is not completely understood, it is hypothesized that the shortening of the anagen phase which occurs in those with androgenic alopecia and the resulting gradual shrinkage of the hair follicle itself while, conversely, the sebaceous glands enlarge, can be delayed or inhibited by chemical intervention to the region's cells with the result that strong blood and oxygen flow is maintained and/or physical or chemical inhibitors to normal cell function and migration are minimized.

Condition and treatment

Androgenic alopecia, an inherited trait that clinically commences with the shedding of over 100 strands per day. The inventor believes that healthy subjects experiencing androgenic alopecia can return to normal shedding rates with regular and sustained usage of the formula at a dose of about 4 to 8 ml per day, applied as a lotion to the scalp morning and evenings preferably after shampooing.

The present invention carries with it none of the health risks associated with Minoxidil use. The ingredients are inexpensive and plentiful and can be manufactured and distributed at a selling price affordable to the vast majority of the 55 million U.S. citizens experiencing androgenic alopecia.

The following examples will serve to further typify the nature of the invention but should not be construed as a limitation on the scope thereof which is defined solely by the appended claims.

EXAMPLE ONE

At the age of 47 female subject noticed the onset of alopecia (a loss of 250 shafts per day). Medical history and blood tests at this onset did not identify a cause other than genetic. The formula was applied topically twice daily and the subject experienced a recovery within six months. She has since maintained a regimen of 1× daily applications and has avoided recurrence of the symptoms.

EXAMPLE TWO

Male Caucasian, aged 48 was experiencing androgenic alopecia for approximately 10 years and had been using Rogaine for at least five of those years. He reported that, while effluvium continued, a 1× per day regimen of Rogaine applications appeared to stall the process somewhat. The subject, however, was experiencing weight gain and decided to discontinue Rogaine usage for this reason. He was also concerned about its long term possible affects on his heart. The subject began 1× daily applications of the formula and reported results identical to Rogaine (1×/day usage), that is, minimum hair loss. When the subject discontinued use of the formula for more than a week he reported higher effluvium rates.

What is claimed is:

1. A composition for the topical treatment of alopecia comprising:

(a) up to about 2% by weight of an agent having at least one of keratolytic or bactericidal activity;

(b) from about 2% to about 5% by weight of liquor carbonis detergens;

(c) from about 3% to about 20% by weight of a rubefacient;

(d) about 7% by weight of an antidessication and/or cornification agent; and (e) from about 60% to about 95% by weight of a pharmaceutically acceptable carrier.

2. A composition according to claim 1 wherein said agent having at least one of keratolytic or bactericidal activity is salicylic acid.

3. A composition according to claim 1 wherein said rubefacient is spirits of camphor.

4. A composition according to claim 1 wherein said antidessication and/or cornification agent is castor oil.

5. A composition according to claim 1 wherein said carrier is isopropyl alcohol.

6. A method for treating alopecia comprising: topically administering a formulation having (a) up to about 2% by weight of an agent having at least one of keratolytic or bactericidal activity;

(b) from about 2% to about 5% by weight of liquor carbonis detergens;

(c) from about 3% to about 20% by weight of a rubefacient;

(d) about 7% by weight of an antidessication and/or cornification agent; and (e) from about 60% to about 95% by weight of a pharmaceutically acceptable carrier.

7. The method of claim 6 wherein said agent having at least one of keratolytic or bactericidal activity is salicylic acid.

8. The method of claim 6 wherein said rubefacient is spirits of camphor.

9. The method of claim 6 wherein said antidessication and/or cornification agent is castor oil.

10. The method of claim 6 wherein said carrier is isopropyl alcohol.

* * * * *